(12) United States Patent
Baldwin et al.

(10) Patent No.: US 8,285,025 B2
(45) Date of Patent: Oct. 9, 2012

(54) METHOD AND APPARATUS FOR DETECTING DEFECTS USING STRUCTURED LIGHT

(75) Inventors: Leo Baldwin, Beaverton, OR (US); Joseph J. Emery, Vancouver, WA (US)

(73) Assignee: Electro Scientific Industries, Inc., Portland, OR (US)

( * ) Notice: Subject to any disclaimer, the term of this patent is extended or adjusted under 35 U.S.C. 154(b) by 1154 days.

(21) Appl. No.: 12/055,052

(22) Filed: Mar. 25, 2008

(65) Prior Publication Data

US 2009/0245614 A1 Oct. 1, 2009

(51) Int. Cl.
*G06K 9/03* (2006.01)
(52) U.S. Cl. ............ 382/141; 382/151; 356/237.2
(58) Field of Classification Search .... 356/237.1–237.5, 356/239.1, 239.7, 239.8; 382/141, 145, 144, 382/149, 195, 218, 224
See application file for complete search history.

(56) References Cited

U.S. PATENT DOCUMENTS

| | | | |
|---|---|---|---|
| 4,741,621 A | 5/1988 | Taft et al. | |
| 4,946,281 A | 8/1990 | Dell'Eva | |
| 5,359,416 A | 10/1994 | Mueller | |
| 5,515,159 A * | 5/1996 | Sites et al. ............... | 356/237.1 |
| 5,535,002 A | 7/1996 | Csipkes | |
| 5,636,020 A | 6/1997 | Csipkes | |
| 6,064,759 A | 5/2000 | Buckley et al. | |
| 6,100,990 A | 8/2000 | Ladewski | |
| 6,577,405 B2 | 6/2003 | Kranz et al. | |
| 6,608,676 B1 * | 8/2003 | Zhao et al. ............... | 356/237.2 |
| 6,788,210 B1 | 9/2004 | Huang | |
| 6,974,964 B1 | 12/2005 | Wang | |
| 7,181,060 B2 * | 2/2007 | Honda et al. ............ | 382/151 |
| 7,187,438 B2 * | 3/2007 | Hamamatsu et al. ...... | 356/237.4 |
| 7,315,643 B2 | 1/2008 | Sakamoto | |
| 7,379,175 B1 * | 5/2008 | Stokowski et al. ........ | 356/237.5 |
| 7,714,997 B2 * | 5/2010 | Shibata et al. ............ | 356/237.2 |
| 2002/0088952 A1 * | 7/2002 | Rao et al. ................ | 250/559.45 |
| 2005/0219518 A1 * | 10/2005 | Korngut et al. ........... | 356/237.2 |
| 2006/0013092 A1 * | 1/2006 | Lee et al. ................. | 369/53.1 |
| 2006/0250612 A1 * | 11/2006 | Meeks ..................... | 356/237.2 |
| 2007/0041609 A1 * | 2/2007 | Chung et al. ............. | 382/100 |
| 2008/0015802 A1 * | 1/2008 | Urano et al. .............. | 702/81 |
| 2008/0085050 A1 * | 4/2008 | Barbu et al. .............. | 382/154 |
| 2008/0117415 A1 * | 5/2008 | Hamamatsu et al. ...... | 356/237.4 |
| 2009/0033924 A1 * | 2/2009 | Uto et al. ................. | 356/237.2 |
| 2010/0128970 A1 * | 5/2010 | Nakagaki et al. ......... | 382/149 |

FOREIGN PATENT DOCUMENTS

| | | |
|---|---|---|
| JP | 07-311017 A | 11/1995 |
| JP | 10-054709 A | 2/1998 |
| JP | 10-300446 A | 11/1998 |
| JP | 2007-040801 A | 2/2007 |

OTHER PUBLICATIONS

International Search Report of PCT/US2009/037940.
The International Preliminary Report on Patentability of PCT/US2009/037940.
Translation of the official letter from Chinese Application No. 2009801104908, 3 pages.

* cited by examiner

*Primary Examiner* — Hoa Pham

(57) ABSTRACT

An improved method and apparatus for detecting problems with fit and finish of manufactured articles is presented which uses structured light. Two or more structured light images acquired from opposing directions is used to measure the fit of mating surfaces while avoiding false positives caused by small defects near the seam.

12 Claims, 8 Drawing Sheets

METHOD AND APPARATUS FOR DETECTING DEFECTS USING STRUCTURED LIGHT

TECHNICAL FIELD

The present invention relates to using machine vision to detect localized detects in manufactured articles. More specifically it relates to using structured light projected onto an article to detect misalignment of mated surfaces while reducing false defects indications caused by small perturbations in the surfaces being inspected.

BACKGROUND OF THE INVENTION

Many articles of manufacture are distinguished by having exterior packaging assembled from two or more components. A feature often desired by the manufacturer is to have the assembled components have the appearance of being seamless. This is achieved by having the components manufactured to tolerances such that when they are assembled, the seam between components is not readily discernable. Problems with this method of assembly arise when, in spite of the tolerances to which the parts were manufactured, small variations arise in the parts to be mated. One solution to this problem is to inspect the articles after they are assembled to determine whether or not the surfaces have mated with acceptable accuracy.

The simplest solution is to have humans inspecting the finished articles by eye to determine if they are acceptable. While humans are relatively easy to train and replace, difficulties with human inspection include inconsistent results over time and difficulties with making quantitative judgments regarding the articles being inspected. For example, a human can be trained to inspect articles by showing them good and bad articles and can then be expected to accept or reject further articles depending upon how much they resemble the examples shown. Difficulty comes, however in that human inspectors make qualitative, rather than quantitative decisions. This makes it very difficult to inspect parts to specific numerical tolerances, meaning that different inspectors may classify the same part differently. This tends to defeat the purpose of inspecting articles to insure uniform appearance. This is especially difficult when the parts happen to be made of differing materials, such as when a plastic part needs to mate with an aluminum part.

To insure uniform appearance and enforce quantitative standards for quality, machine vision systems can be used to inspect articles. 2D machine vision systems which rely on color or grayscale images have the same difficulties that humans do in quantitatively measuring anomalies in surface mating applications. For this reason 3D vision is sometimes used to inspect surfaces. There are many different methods of extracting 3D information from surfaces, each of which varies with regard to resolution, accuracy and speed. The subset of 3D measurement methods most suited to solving this surface inspection problem involve projecting patterns of light ("structured light") on a surface and measuring the local displacements of the pattern to extract 3D information about the surface.

Structured light can be created on the surface of an article in several different ways. The methods we are interested in project an in-focus pattern onto the surface and then extract information about the surface by acquiring an image or images of the pattern, measuring the 2D location of portions of the pattern and calculating the height of the point geometrically. A schematic diagram of a prior art structured light system is shown in FIG. 1. Structured light projector 2 projects structured light 4 onto an article 6, where it is imaged by a camera 8 to form an image 10 which is acquired and processed by computer 12. FIG. 2 shows an example of how a prior art structured light system can form an image of a discontinuous edge on an article. In this diagram, a structured light projector 14 projects stripes 16 onto an article 18 which is composed of an upper surface 20 and a lower surface 22. The stripes 16 are projected onto the surfaces 20 and 22 to form the projected patterns 24 and 26. These patterns 24 and 26 are imaged by the camera 28 and subsequently acquired by the computer 30 to form an image 32 to be subsequently processed by the computer 30. The image 32 shows schematically how the discontinuity between surfaces 20 and 22 shows up as a displacement between groups of imaged lines 34 and 36. Computer 30 typically uses the displacement of the structured light to determine the relative altitude of a portion of an article.

FIG. 3 is a schematic diagram illustrating how a prior art structured light system can be used to calculate the relative altitude of points on surfaces based on geometry. In FIG. 3, a structured light projector 40 projects lines, one of which is shown 42. This line extends into and out of the plane of the drawing and impinges an article 52 having two surfaces 44 and 46 much like the article in FIG. 2. Light from the line 62 is reflected from the article 68 is imaged by a camera/lens system (not shown) onto an image sensor plane 54. In this case the image sensor plane 54 would intersect the light 48 reflected from surface 44 at point 56 and light 50 reflected from surface 46 at point 58. Note that the difference in altitude between surfaces 44 and 46, marked as "B" in FIG. 3 results in a difference between points 56 and 58 on the image sensor plane 54 marked as "A" in the image plane. In practice, well known machine vision techniques can be used to determine the location of points 56 and 58 in the image plane and measure the distance A. In this example the distance A is related to the distance B by the equation $$A = B(1+\tan(a)/\tan(b)) \quad \quad 1)$$

Where a and b are the angles indicated in FIG. 3 as the illumination and viewing angles respectively.

One example of this method is described in U.S. Pat. No. 6,064,759 by inventors B. Shawn Buckley, et al. In this example, a single camera position is used to acquire an image of the structured light projected onto a surface following which geometric models are fit to the surface. Multiple points in the surface image are used to form a single 3D point, which improves the accuracy of the measurement.

A similar method described in "Technique for Phase Measurement and Surface Reconstruction by Use of Colored Structured Light", by Oleksandr, et al, (Applied Optics Vol. 41, Issue 29, pp 6104-6117 (2002)), projects multiple colored patterns to distinguish the projected light and attempt to improve the accuracy of the 3D measurements. They discuss using structured light to determine the topography of an automotive windshield using differential equations to extract 3D information from the structured light images.

Two problems exist with these methods. The first is speed. Creating a 3D map of an entire surface is time consuming. In the application we are contemplating herein, we are not interested in the entire surface, only the small area adjacent to the seam between components. Prior art methods are aimed at characterizing an entire surface or article, rather than solely extracting information regarding the mating of two surfaces. Thus far more calculations are performed by prior art systems than are desired for this application.

The second problem is illustrated by FIG. 4. In FIG. 4, a structured light projector 60 projects a pattern consisting of lines onto an article 68, one of which is shown 62. The line of light 62 intersects the article 68 at two surfaces 64, 66. The light intersecting the surfaces is imaged by a camera/lens system (not shown) onto the image plane of the sensor 76. Light from the stripe 62 is reflected by the top surface 66 to form light ray 70 which intersects the image sensor plane 76 at point 78. In this example, light reflecting off the bottom surface 64 deviates from the expected direction onto a new direction 74 as a result of a small defect in the surface 72, causing the light ray 74 to intersect the image sensor plane 76 at point 80. This results in a measured distance A when machine vision techniques are used to measure the distance between points 78 and 80 on the image sensor plane. If the calculations shown in equation 1, above, were applied to measurement C with the expectation that distance D could be accurately estimated, an error would occur. In the instant application, we are interested in both detecting small defects in the surfaces and distinguishing them from more systematic differences in surfaces caused by mis-mated surfaces. The methods mentioned above would either filter the localized defects out or fold them into the calculation, making them indistinguishable from systematic differences between mating surfaces. Neither of these results is desirable for the instant application. For these reasons, there is a need for a method for efficiently and accurately detecting mis-mated surfaces using structured light while rejecting false positives caused by localized defects.

SUMMARY OF THE INVENTION

An object of the present invention is, therefore, to provide a method and apparatus in the form of a structured light machine vision system with improved ability to detect variations in mating between two surfaces while ignoring anomalies caused by small defects in either surface, and to perform these tasks with less computation than prior art systems. To achieve the foregoing and other objects in accordance with the purposes of the present invention, as embodied and broadly described herein, a method and apparatus is disclosed.

An embodiment of this invention uses two cameras viewing an article from two different directions each viewing an article illuminated by separate structured light projectors. A schematic diagram of this system is shown in FIG. 5. In this embodiment, a first structured light projector 90 projects a first structured light pattern 92 onto an article 94, whereupon a first camera 96 forms an image of the structured light pattern 92 which is then acquired and processed by the computer 95. Subsequently, the second structured light projector 97 projects a second structured light pattern 98 onto an article 94, whereupon it is imaged by a second camera 99 and then acquired and processed by the computer 95. This embodiment can separate true differences in altitude between surfaces from localized defects due to the fact that surfaces will appear to have the same relative altitude with respect to another surface regardless of the direction it is viewed from, while a localized defect will likely appear to change in altitude when viewed from different angles. This is illustrated in FIGS. 6 and 7. In FIG. 6, two structured light projectors 100, 104 illuminate an article 108 from opposite directions. The altitude difference between surfaces 110 and 112 as measured at image sensor planes 122 and 124 are substantially the same. Looking at FIG. 7, we can see that in the presence of a local defect 158, image sensors at 148 and 154 measure different values for the altitude of surface 140 relative to surface 142.

The algorithm for detecting localized flaws involves acquiring structured light images from two different directions. Typically the two directions are 180 degrees apart and both structured light projectors and cameras are at the same angle with respect to the article, but this is not required. Having the cameras and projectors set up symmetrically makes the calculations somewhat simpler and will be used herein to illustrate the methods without loss of generality. Each camera and structured light projector pair should be aligned so as to be able to view significant portions of the reflection of the structured light projected onto the article. In particular, both cameras should be able to view portions of the structured light projected onto the areas of the article where inspection is desired.

An aspect of the instant invention is that once acquired, the structured light images are typically not processed to yield global information regarding the article being inspected. Calculation time can be decreased by use of a priori information regarding the location of the article and the location of the area on the article to be inspected. Knowledge of the location of the area to be inspected allows the method to calculate only those data points that will be required to make a determination regarding the quality of the seam or seams between two or more components that comprise an article. This method assumes that information regarding the location of the article in the fields of view and the location of the seams to be inspected is known. This can be assured by holding the article to be inspected in a fixture with a known location with respect to the camera and light projectors. In addition, information regarding the location to be inspected on the article can be pre-programmed from engineering drawings or other information about the article, or can be deduced from test images of the structured light pattern on the articles. As an alternative to the above methods, well-known machine vision techniques could be used to locate the article and thereby locations to be inspected in cases where the article is not fixtured or otherwise positioned in a known location prior to inspection. This location step could be performed using the projected structured light or another non-structured light source.

DETAILED DESCRIPTION OF PREFERRED EMBODIMENTS

Product appearance is very important to any company selling products. One very important aspect of product appearance is "fit and finish", which refers to the overall perceived quality of the product. High quality fit and finish can increase a products perceived value and thereby increase sales and profit margins, and is therefore justifiably desired by manufacturers. A particularly difficult aspect of fit and finish is the mating of components to form a continuous surface, where the seam between the components is designed to be nearly invisible to the user. This is difficult to achieve with normal manufacturing tolerances and to insure that all products meet established standards for fit and finish, products are typically inspected.

Fit and finish inspection for mated surfaces requires that subtle differences in surface height be detected. These differences may not be readily discerned visually, but rather apparent only when, for instance, the surface is inspected by running a human finger over the seam. What this means is that usual 2D machine vision techniques cannot be used effectively to detect flaws in mated surfaces.

A variety of 3D vision techniques are available, however, two factors existing 3D vision techniques less desirable for this type of application. The first is speed. In general, 3D vision techniques are used to characterize entire articles or surfaces. In this instance we are only interested in inspecting a single aspect of an article, namely quantifying the fit between two surfaces along a seam where two components are mated. Typical 3D applications calculate far more data points than are required to obtain the information we are interested in. Thus the instant invention, which calculates only data points in the vicinity of the seam, offers higher performance than traditional 3D vision methods.

Another problem is that articles to be inspected sometimes exhibit small flaws in the vicinity of the seam to be inspected that can be mistaken for mis-mated components. Typically, 3D inspection programs have steps that either average the flaw's value into a larger area or filter it out completely. The instant invention improves this by distinguishing between small imperfections in the surface and actual differences in relative altitude between surfaces.

Figure 5:
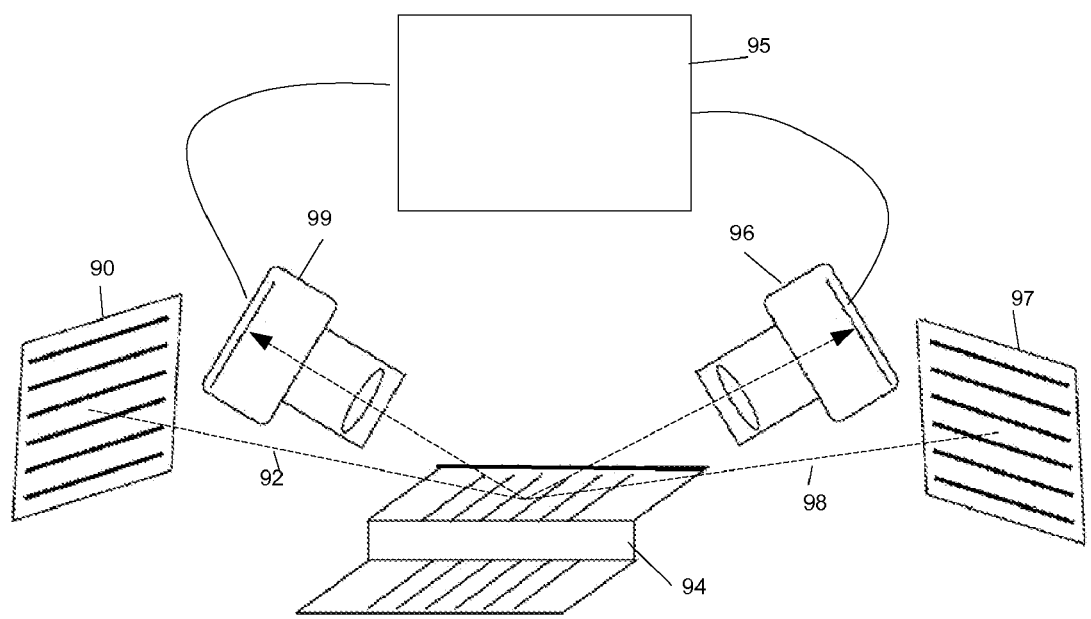
FIG. 5 is a schematic diagram of a structured light system.
Figure 6:
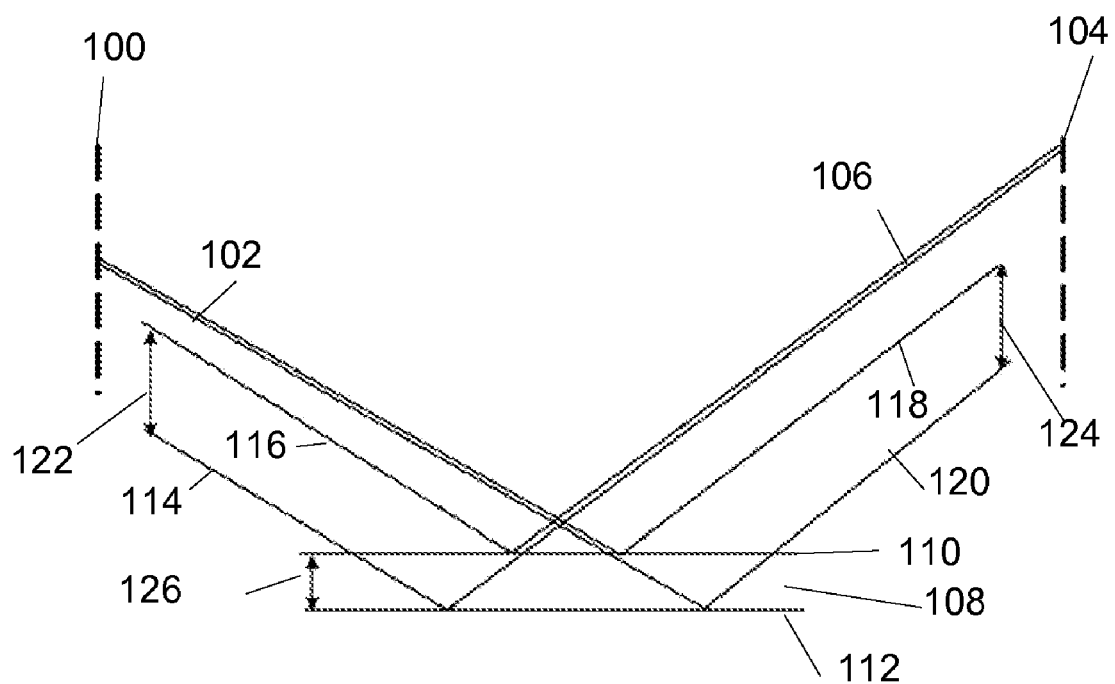
FIG. 6 is a diagram showing the symmetry of a mismatched edge detected by a structured light system.
Figure 7:
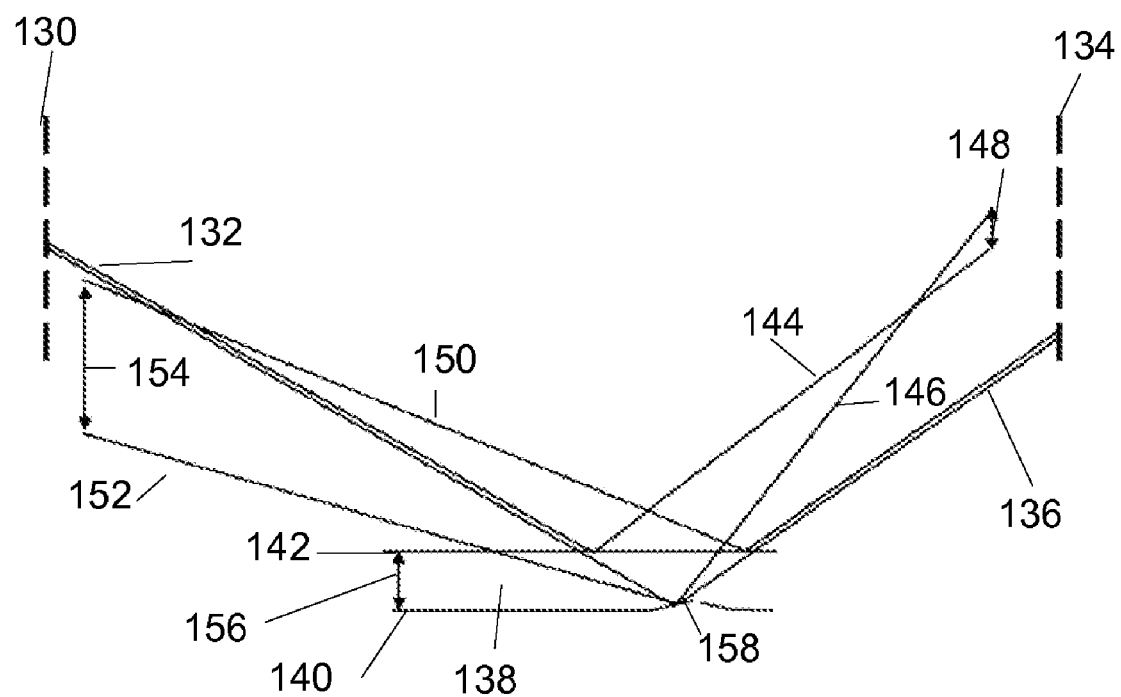
FIG. 7 is a diagram showing the asymmetry of a localized defect detected by a structured light system.

FIG. 5 is a schematic diagram of one embodiment of the instant invention. A first structured light projector 90 projects 92 a first in focus structured light pattern onto an article 94. This first structured light pattern is imaged by a first camera 96 and acquired by a computer 95 for subsequent processing. A second structured light projector 97 projects a second in focus structured light pattern 98 onto the same area on an article 94 where it is imaged by a camera 99 and then acquired by a computer 95 and processed. In this embodiment, the optical axes of the projectors and cameras are arranged in a plane generally perpendicular to the planes formed by the surfaces to be inspected. This arrangement is not required by the instant invention, but does make the calculations somewhat easier and hence quicker to perform. In practice, the projector could be at almost any angle as long as the light can reach the surface without being blocked by parts of the object. The resolution of the system will be dependent upon the angle of the structured light projector with respect to the surface to be inspected, with a tradeoff between resolution and accuracy as the projector angle is moved from a large angle where the projector is looking down almost perpendicular to the surface to a grazing angle where the projector angle is nearly parallel to the surface. For this embodiment, the projector angle is between 30 and 60 degrees from the surface, most preferably at 45 degrees to the surface. The camera is then placed opposite to the projector at an angle that is similar to the angle of the projector. Note that the camera can be placed at any angle that can see the structured light clearly, but the same trade offs exist with regard to resolution vs. accuracy.

In this embodiment the second projector and camera are arranged symmetrically with the first projector and camera, in the same vertical plane and 180 degrees opposed to the first projector and camera. This configuration is convenient and makes calculations simpler, but the second projector and camera can be at any angle, as long as the areas of interest on the surface are illuminated by both projectors and able to be viewed by both cameras.

In this embodiment, the structured light projectors and cameras alternate in projecting their patterns and acquiring images so as not interfere with each other. Other schemes for keeping the patterns separate are possible. In other embodiments, the patterns could be projected using different wavelengths of light and optical filters placed on the cameras to differentiate between the patterns. Similarly, the patterns could be projected using orthogonal polarizations, with analyzers on the cameras to separate the patterns. What these embodiments have in common is that they allow the patterns to be acquired simultaneously rather than serially. In addition, the optics used to project the structured light pattern onto the article and/or the optics used by the camera to image the structured light pattern may be designed to suppress details like surface finish of the parts and to enhance the details of the structured light pattern. For example, the projector may project the pattern using infrared light and the camera may have filters to eliminate all but infrared light from the image.

Figure 1:
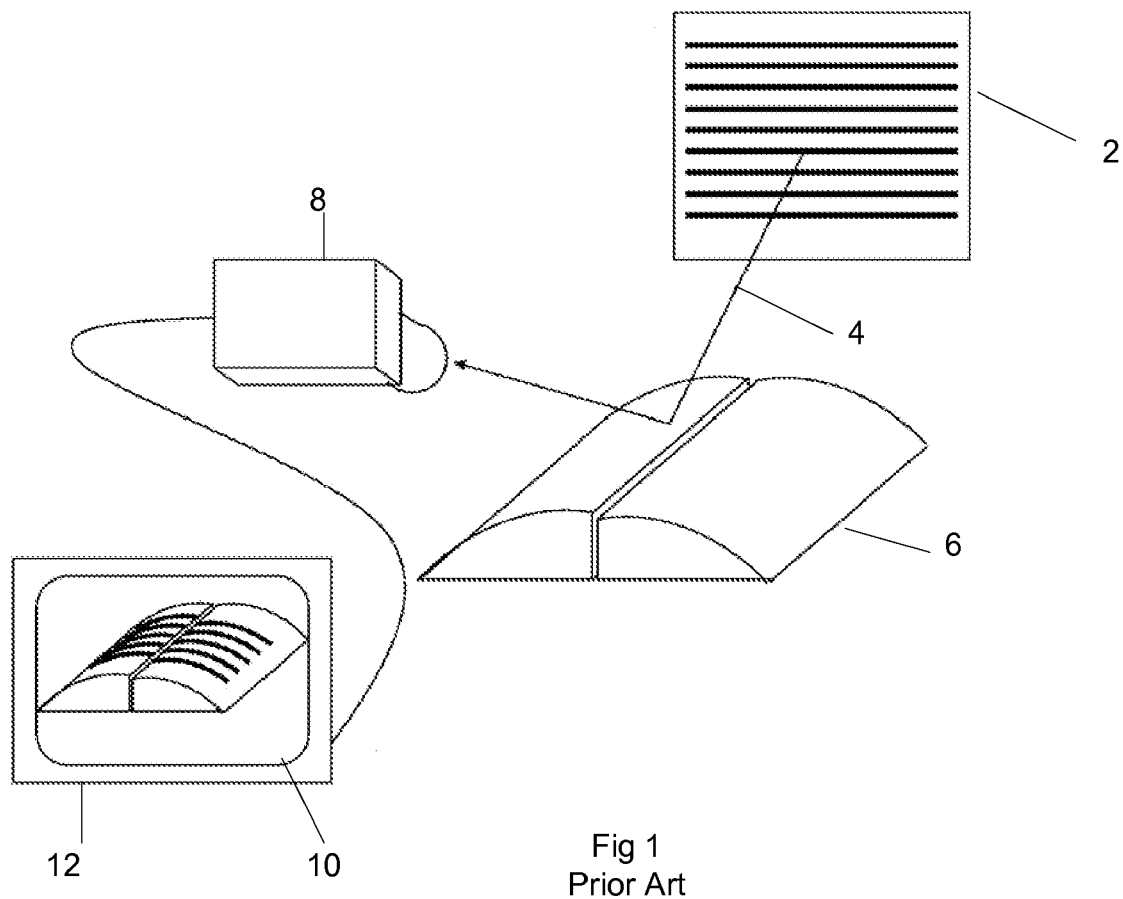
FIG. 1 is a schematic diagram of a prior art structured light system.
Figure 2:
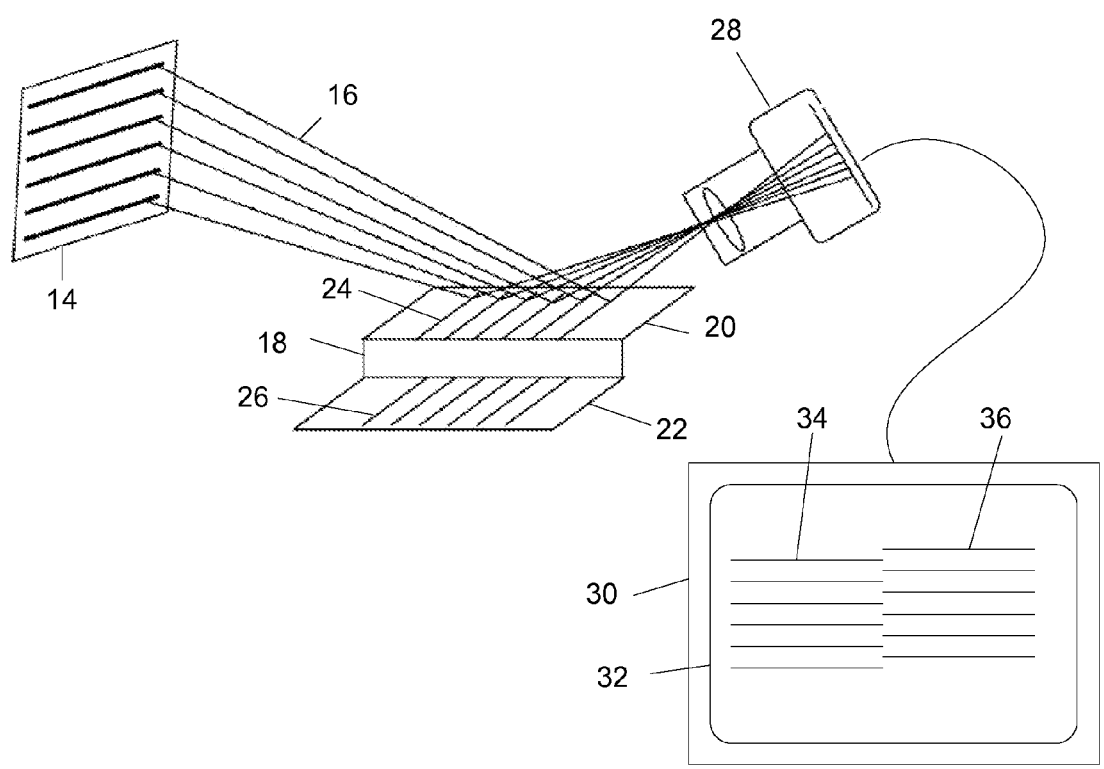
FIG. 2 is a schematic diagram of a prior art structured light system showing the relationship between projected light and an image
Figure 3:
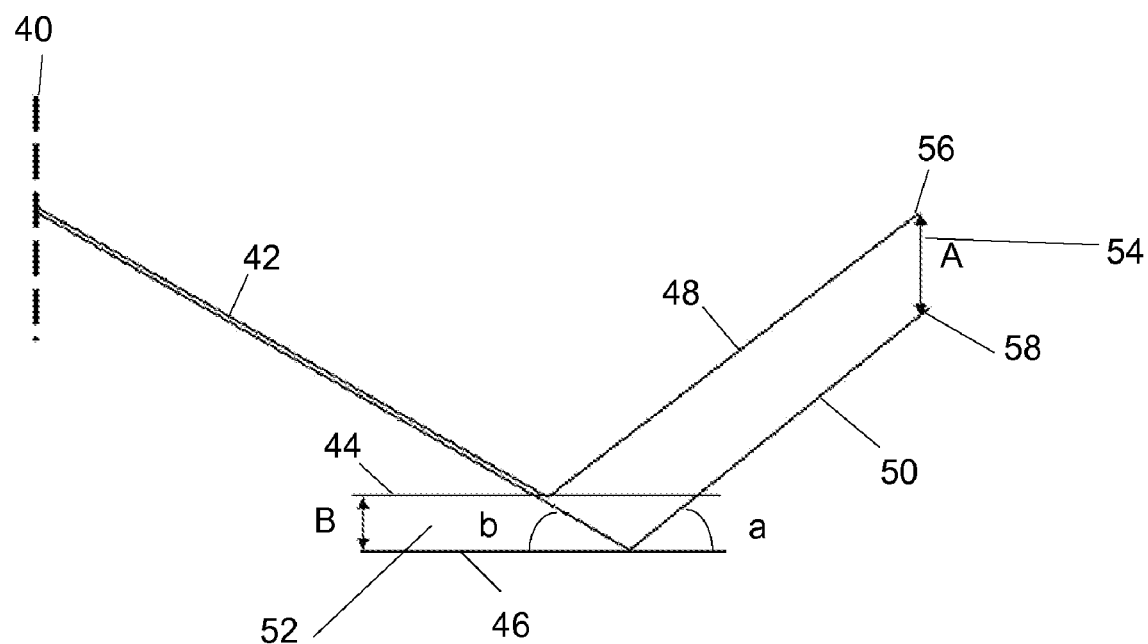
FIG. 3 is a diagram showing how a mis-mated edge is detected by a structured light system
Figure 4:
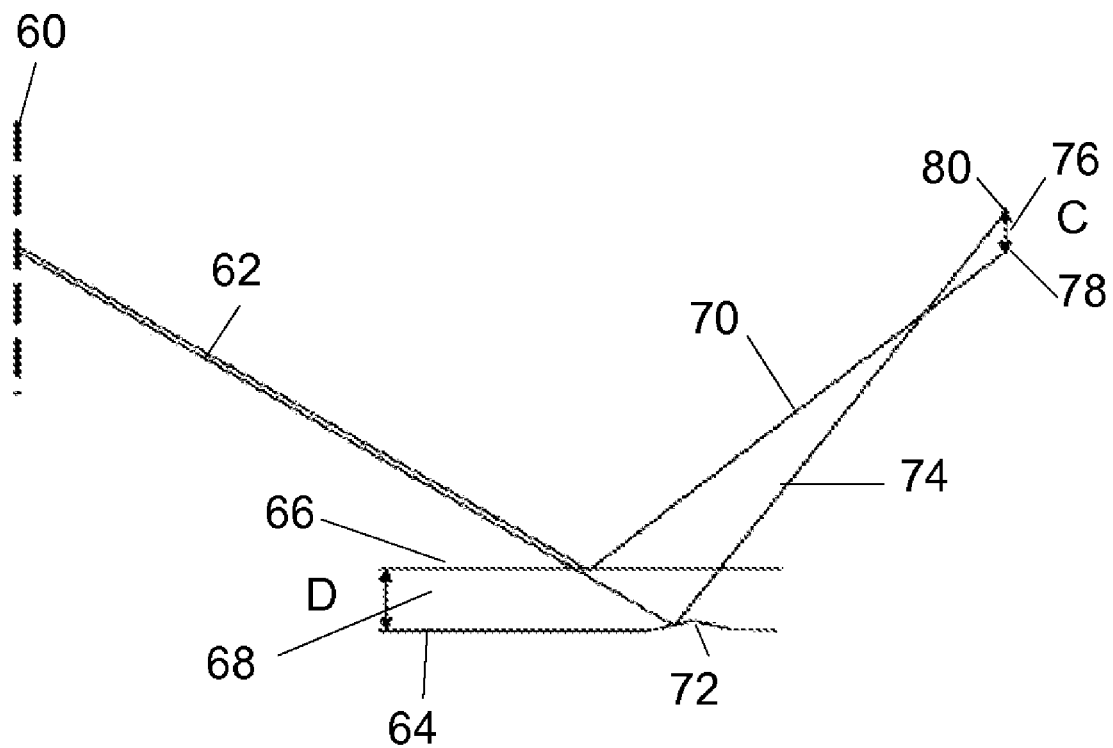
FIG. 4 is a diagram showing how a localized defect is detected by a structured light system
Figure 8:
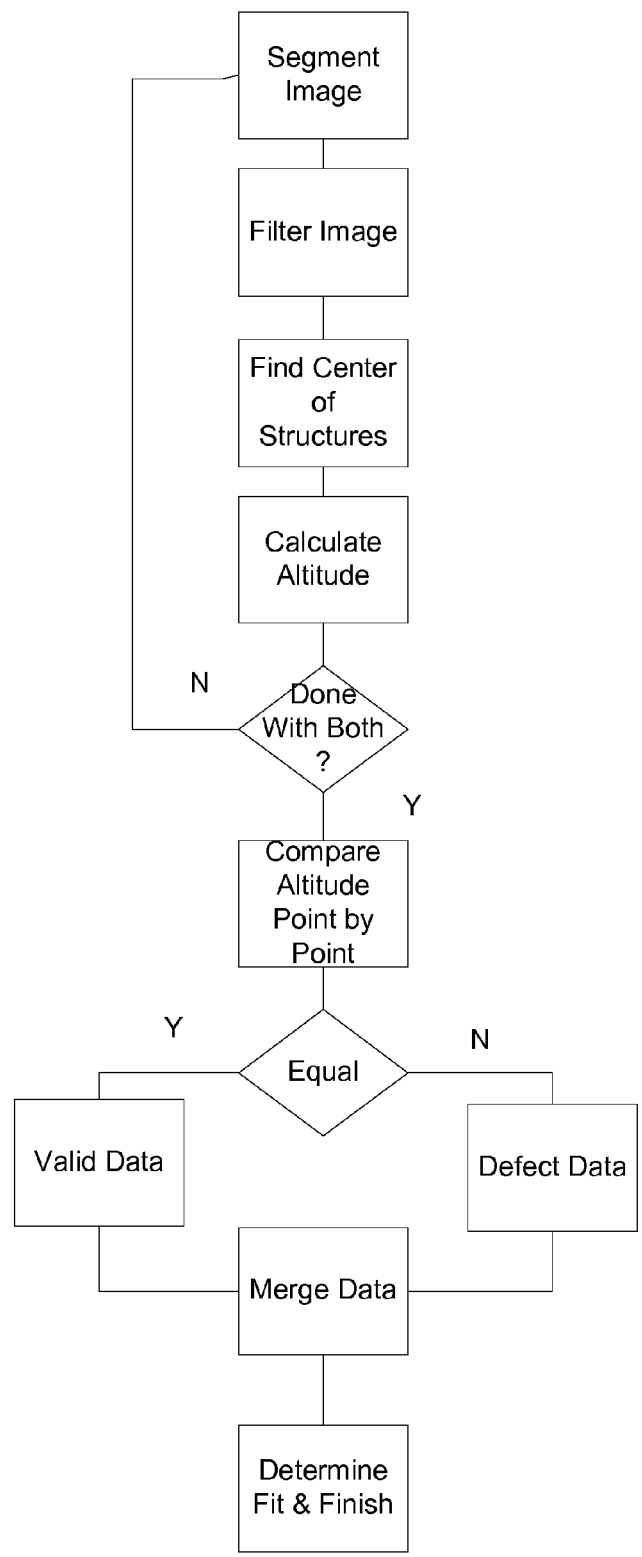
FIG. 8 is a flow diagram of an algorithm used to detect defects using a structured light system.

The algorithm used to process the data in one embodiment of this invention is shown in FIG. 8. After the image data are acquired by the computer, processing starts by identifying the region or regions in the image to be processed. This allows the algorithm to process only those regions that will contribute to the desired result thereby increasing system throughput. Once the regions are selected, the image data is typically filtered to reduce noise. After filtering, the structured light features in the image are detected with high precision. For example, if the structured light features are lines, well known machine vision algorithms can be used to detect the center of the lines with sub-pixel precision. Following the high-precision detection of the feature, the altitude of the surface under the feature can be deduced. One method of doing this is illustrated in FIG. 3 and described by equation 1, above. Assuming that surface 44 is selected as the origin for altitude measurement, measurement of the location of the stripe 42 will be offset by and amount A in the image. After calculation with equation 1, the altitude of stripe 42, and hence surface 46 of article 52 will be established as −B from the arbitrarily chosen origin 44.

Determination of fit and finish from this data depends on two subsequent analysis steps. First the image data is merged. In most cases, the two data sets will be identical. In these cases, the output data would be either of the input pixels. In cases where the input altitude measurements are unequal, the output pixel will be flagged and the magnitude of the difference will be noted. In cases where the pixels are identical, the area on either side of the known location of the seam will be inspected to determine if they are close enough to pass inspection. If they are different, meaning a difference in surface location exists, the difference is noted and passed onto other parts of the program for a decision as to whether or not the article passes inspection. In the case where the values differ, it is noted that the location does not mean that the surfaces are at different altitudes, but rather that there is a surface imperfection that prevents the system from making a valid measurement. The program must then decide if the imperfection is large enough to warrant rejection or possibly if the article should be inspected by a human to determine its acceptability.

Many different patterns of structured light could be used to illuminate articles to extract the information desired. One embodiment uses stripes projected onto the surface perpendicular to the seam to be inspected to detect changes in altitude on either side of the seam. Other patterns could be used, for instance a pattern of dots projected on the surface. Nearly any pattern could be used, as long as it was able to be imaged cleanly, the pattern elements could be located with sub-pixel accuracy and the elements could be correctly identified in the image.

Another embodiment of the instant invention would use a single structured light projector and camera pair in an opposed arrangement. In this embodiment, the projector/camera pair acquires a first image of the article, then the article is rotated with respect to the projector/camera pair and another image acquired. Either the article, the projector/camera pair or both may be rotated in order to acquire opposing views of the article for processing. Once the images are acquired, processing proceeds as described above.

Further embodiments involve taking more images from more angles to over determine the altitude of surfaces and improve the accuracy of the measure. Also, the structured light pattern can be indexed across the surface and multiple images acquired in order to increase the sample density of the surface measurements.

It will be apparent to those of ordinary skill in the art that many changes may be made to the details of the above-described embodiments of this invention without departing from the underlying principles thereof. The scope of the present invention should, therefore, be determined only by the following claims.

We claim:

1. An improved method for classifying defects in an article, including projecting light patterns onto said article, acquiring images of said projected pattern, transmitting said images to a computer, and processing said images with said computer, the improvement comprising:
   projecting a first light pattern onto said article from a first direction;
   acquiring a first image of said first light pattern with an image sensor;
   transmitting said first image from said sensor to said computer;
   projecting a second light pattern onto said article from a second direction;
   acquiring a second image of said second pattern with an image sensor;
   transmitting said second image from said image sensor to said computer; and
   processing said first and second images with said computer to detect differences between the images and thereby classify defects in the article,
   wherein acquiring the first image includes acquiring an image of the first light pattern projected onto the article and reflected by the article along a third direction relative to a location on the article,
   wherein acquiring the second image includes acquiring an image of the second light pattern projected onto the article and reflected by the article along a fourth direction relative to the location on the article, and
   wherein the third direction is different from the fourth direction.

2. The method of claim 1 wherein said first direction and said second direction are opposing views.

3. The method of claim 1 wherein said first and said second light patterns are the same.

4. The method of claim 1 wherein acquiring said first and second images comprises acquiring said first and second images with a single image sensor.

5. The method of claim 1 wherein the first light pattern comprises structured light.

6. The method of claim 1 wherein the second light pattern comprises structured light.

7. An improved method for classifying defects in an article, including projecting light patterns onto said article, acquiring images of said projected pattern with an image sensor, transmitting said images to a computer, and processing said images with said computer, the improvement comprising:
   projecting a light pattern onto said article and acquiring a first image of said light pattern with an image sensor;
   transmitting said first image from said image sensor to said computer;
   rotating said article;
   projecting said light pattern onto said rotated article and acquiring a second image of said light pattern with said image sensor;
   transmitting said second image from said image sensor to said computer; and
   processing said first and second images with said computer to detect differences between the images and thereby classify defects in the article.

8. The method of claim 7 wherein said article is rotated 180 degrees.

9. The method of claim 7 wherein the light pattern comprises structured light.

10. An improved system for classifying defects in an article with projected light patterns, image sensors and computers, the improvement comprising:
    first and second patterned light projectors arranged adjacent to different portions of the article to project light patterns onto substantially the same location on said article from different directions;
    first and second image sensors arranged to acquire first and second images of said projected light patterns from different directions; and
    a computer communicating with first and second image sensors to process the acquired first and second images to detect differences between the first and second images and thereby classify defects.

11. The system of claim 10 wherein said first direction and said second direction are opposing views.

12. The system of claim 10 wherein the projected light patterns comprise structured light.

* * * * *